(12) United States Patent
Shakespeare et al.

(10) Patent No.: US 8,401,809 B2
(45) Date of Patent: Mar. 19, 2013

(54) SYSTEM AND METHOD FOR ADJUSTING AN ON-LINE APPEARANCE SENSOR SYSTEM

(75) Inventors: Tarja T. Shakespeare, Hiltuianlahti (FI); John F. Shakespeare, Hiltulanlahti (FI)

(73) Assignee: Honeywell International Inc., Morristown, NJ (US)

( * ) Notice: Subject to any disclaimer, the term of this patent is extended or adjusted under 35 U.S.C. 154(b) by 311 days.

(21) Appl. No.: 12/834,667

(22) Filed: Jul. 12, 2010

(65) Prior Publication Data
US 2012/0010841 A1    Jan. 12, 2012

(51) Int. Cl.
*G01D 18/00* (2006.01)
*G06F 19/00* (2006.01)

(52) U.S. Cl. ......... 702/104; 356/402; 702/159; 702/172

(58) Field of Classification Search .................... 702/85, 702/104, 116, 117, 127, 188, 159, 172; 250/559.01; 356/72, 73, 328, 402, 425, 589
See application file for complete search history.

(56) References Cited

U.S. PATENT DOCUMENTS

| | | | |
|---|---|---|---|
| 3,536,405 A | 10/1970 | Flower |
| 3,802,774 A | 4/1974 | Eschler et al. |
| 4,006,358 A | 2/1977 | Howarth |
| 4,068,955 A | 1/1978 | Bodlaj |
| 4,159,874 A | 7/1979 | Dearth et al. |
| 4,160,204 A | 7/1979 | Holmgren et al. |
| 4,276,480 A | 6/1981 | Watson |
| 4,288,691 A | 9/1981 | Horton |
| 4,311,658 A | 1/1982 | Nicoll |
| 4,376,946 A | 3/1983 | Kaminow et al. |
| 4,439,038 A | 3/1984 | Mactaggart |
| 4,490,845 A | 12/1984 | Steinbruegge et al. |
| 4,505,550 A | 3/1985 | Steinbruegge |
| 4,565,444 A | 1/1986 | Mactaggart |
| 4,592,043 A | 5/1986 | Williams |
| 4,634,928 A | 1/1987 | Figueroa et al. |
| 4,653,925 A | 3/1987 | Thornton, Jr. |

(Continued)

FOREIGN PATENT DOCUMENTS

| | | |
|---|---|---|
| DE | 3148076 A1 | 6/1983 |
| DE | 19515499 A1 | 10/1996 |

(Continued)

OTHER PUBLICATIONS

Communication pursuant to Article 94(3) EPC dated Sep. 29, 2011 in connection with European Patent Application No. 11 172 011.6.

(Continued)

*Primary Examiner* — John H Le (57) ABSTRACT

A system, apparatus and method are provided for adjusting an on-line appearance sensor system (OnLASS) for color and other appearance characteristic(s) of a web product produced during a production run of a web production system. The OnLASS is calibrated and its setting(s) are sent to a color error minimizer (CEM). The OnLASS measures a first appearance characteristic of the web product during the production run and the on-line measurement is sent to the CEM. After the production run, a second appearance characteristic of the web product is measured with an off-line appearance sensor system (OffLASS) and the off-line measurement is sent to the CEM. The CEM compares the on-line and off-line appearance measurements and adjusts at least one setting based on the comparison. The adjusted setting(s) are sent to the OnLASS.

23 Claims, 4 Drawing Sheets

U.S. PATENT DOCUMENTS

| | | | |
|---|---|---|---|
| 4,699,510 A | 10/1987 | Alguard |
| 4,708,483 A | 11/1987 | Lorenz |
| 4,715,715 A | 12/1987 | Howarth et al. |
| 4,773,760 A | 9/1988 | Makkonen |
| 4,786,817 A | 11/1988 | Boissevain et al. |
| 4,797,246 A | 1/1989 | Reinke et al. |
| 4,807,630 A | 2/1989 | Malinouskas |
| 4,843,481 A | 6/1989 | Plummer |
| 4,856,014 A | 8/1989 | Figueroa et al. |
| 4,879,471 A | 11/1989 | Dahlquist |
| 4,883,963 A | 11/1989 | Kemeny et al. |
| 4,885,709 A | 12/1989 | Edgar et al. |
| 4,928,013 A | 5/1990 | Howarth et al. |
| 5,013,403 A | 5/1991 | Chase |
| 5,015,099 A | 5/1991 | Nagai et al. |
| 5,039,855 A | 8/1991 | Kemeny et al. |
| 5,047,652 A * | 9/1991 | Lisnyansky et al. ..... 250/559.01 |
| 5,094,535 A | 3/1992 | Dahlquist et al. |
| 5,122,974 A | 6/1992 | Chance |
| 5,137,364 A | 8/1992 | McCarthy |
| 5,166,748 A | 11/1992 | Dahlquist |
| 5,172,005 A | 12/1992 | Cochran et al. |
| 5,210,593 A | 5/1993 | Kramer |
| 5,230,923 A | 7/1993 | Hirokawa et al. |
| 5,235,192 A | 8/1993 | Chase et al. |
| 5,276,327 A | 1/1994 | Bossen et al. |
| 5,313,187 A | 5/1994 | Choi et al. |
| 5,338,361 A | 8/1994 | Anderson et al. |
| 5,365,084 A | 11/1994 | Cochran et al. |
| 5,400,258 A | 3/1995 | He |
| 5,438,406 A | 8/1995 | Puschell |
| 5,444,528 A | 8/1995 | Puschell |
| 5,492,601 A | 2/1996 | Ostermayer et al. |
| 5,541,413 A | 7/1996 | Pearson et al. |
| 5,581,353 A | 12/1996 | Taylor |
| 5,598,266 A | 1/1997 | Cornuejols |
| 5,606,173 A | 2/1997 | Concannon et al. |
| 5,642,189 A | 6/1997 | Alguard |
| 5,642,192 A | 6/1997 | Gordon et al. |
| 5,694,214 A | 12/1997 | Watanabe et al. |
| 5,696,591 A | 12/1997 | Bilhorn et al. |
| 5,714,763 A | 2/1998 | Chase et al. |
| 5,774,213 A | 6/1998 | Trebino et al. |
| 5,793,486 A | 8/1998 | Gordon et al. |
| 5,795,394 A | 8/1998 | Belotserkovsky et al. |
| 5,821,536 A | 10/1998 | Pettit |
| 5,891,306 A | 4/1999 | Chase et al. |
| 5,933,243 A | 8/1999 | Hagen |
| 5,963,333 A | 10/1999 | Walowit et al. |
| 5,992,318 A | 11/1999 | DiBello et al. |
| 6,020,959 A | 2/2000 | Imura |
| 6,031,233 A | 2/2000 | Levin et al. |
| 6,038,028 A | 3/2000 | Grann et al. |
| 6,058,201 A | 5/2000 | Sikes et al. |
| 6,074,483 A | 6/2000 | Belotserkovsky et al. |
| 6,088,117 A | 7/2000 | Imura et al. |
| 6,100,986 A | 8/2000 | Rydningen |
| 6,111,649 A | 8/2000 | Tominaga et al. |
| 6,262,419 B1 | 7/2001 | Huth-Fehre et al. |
| 6,263,291 B1 | 7/2001 | Shakespeare et al. |
| 6,272,440 B1 | 8/2001 | Shakespeare et al. |
| 6,281,679 B1 | 8/2001 | King et al. |
| 6,289,600 B1 | 9/2001 | Watts |
| 6,297,879 B1 | 10/2001 | Yang et al. |
| 6,327,374 B1 | 12/2001 | Piironen et al. |
| 6,441,905 B1 | 8/2002 | Tojyo et al. |
| 6,459,488 B1 | 10/2002 | Heffner |
| 6,466,839 B1 | 10/2002 | Heaven et al. |
| 6,476,920 B1 | 11/2002 | Scheiner et al. |
| 6,494,446 B1 | 12/2002 | Tomiyama et al. |
| 6,499,402 B1 | 12/2002 | Sikes et al. |
| 6,515,746 B2 | 2/2003 | Opsal et al. |
| 6,535,278 B1 | 3/2003 | Imura |
| 6,556,305 B1 | 4/2003 | Aziz et al. |
| 6,556,306 B2 | 4/2003 | Jiang et al. |
| 6,559,944 B1 | 5/2003 | Van Aken et al. |
| 6,565,343 B1 | 5/2003 | Krycki |
| 6,573,999 B1 | 6/2003 | Yang |
| 6,584,435 B2 | 6/2003 | Mestha et al. |
| 6,603,551 B2 | 8/2003 | Mestha et al. |
| 6,639,201 B2 | 10/2003 | Almogy et al. |
| 6,643,060 B2 | 11/2003 | Hashimoto et al. |
| 6,646,752 B2 | 11/2003 | Chen et al. |
| 6,690,357 B1 | 2/2004 | Dunton et al. |
| 6,700,370 B2 | 3/2004 | Chen et al. |
| 6,724,473 B2 | 4/2004 | Leong et al. |
| 6,731,380 B2 | 5/2004 | Amara et al. |
| 6,743,337 B1 | 6/2004 | Ischdonat |
| 6,744,052 B1 | 6/2004 | Petersson et al. |
| 6,757,069 B2 | 6/2004 | Bowles |
| 6,760,103 B2 | 7/2004 | Shakespeare et al. |
| 6,762,846 B1 | 7/2004 | Poris |
| 6,763,322 B2 | 7/2004 | Potyrailo et al. |
| 6,780,284 B2 | 8/2004 | Almi et al. |
| 6,793,854 B1 | 9/2004 | Kirjavainen |
| 6,805,899 B2 | 10/2004 | MacHattie et al. |
| 6,816,636 B2 | 11/2004 | Cole et al. |
| 6,822,785 B1 | 11/2004 | Chu et al. |
| 6,849,844 B2 | 2/2005 | Khoury |
| 6,856,436 B2 | 2/2005 | Brukilacchio et al. |
| 6,949,734 B2 | 9/2005 | Neff et al. |
| 7,069,186 B2 * | 6/2006 | Jung et al. ..................... 702/188 |
| 7,116,336 B2 | 10/2006 | Van Aken et al. |
| 7,259,853 B2 | 8/2007 | Hubble, III et al. |
| 7,291,856 B2 | 11/2007 | Haran et al. |
| 7,369,240 B1 | 5/2008 | Abbott et al. |
| 7,466,417 B2 | 12/2008 | Ehbets et al. |
| 7,502,099 B2 | 3/2009 | Imura |
| 7,589,837 B2 | 9/2009 | Wang et al. |
| 7,688,447 B2 | 3/2010 | Shakespeare et al. |
| 2003/0007161 A1 | 1/2003 | Bowles |
| 2003/0058441 A1 | 3/2003 | Shakespeare et al. |
| 2004/0119781 A1 | 6/2004 | Szumla |
| 2004/0124366 A1 | 7/2004 | Zeng et al. |
| 2004/0212804 A1 | 10/2004 | Neff et al. |
| 2004/0246493 A1 | 12/2004 | Kim et al. |
| 2004/0260520 A1 | 12/2004 | Braendle et al. |
| 2005/0065400 A1 | 3/2005 | Banik et al. |
| 2005/0187478 A1 | 8/2005 | Beaudry et al. |
| 2005/0236481 A1 | 10/2005 | Gascoyne et al. |
| 2006/0028156 A1 | 2/2006 | Jungwirth |
| 2006/0132777 A1 | 6/2006 | Hubble et al. |
| 2006/0132796 A1 | 6/2006 | Haran |
| 2006/0132808 A1 | 6/2006 | Jasinski et al. |
| 2006/0164643 A1 | 7/2006 | Giakos |
| 2006/0243931 A1 | 11/2006 | Haran et al. |
| 2007/0027651 A1 * | 2/2007 | Ng et al. ..................... 702/116 |
| 2007/0139735 A1 | 6/2007 | Shakespeare et al. |
| 2007/0144388 A1 | 6/2007 | Shakespeare et al. |
| 2007/0153277 A1 | 7/2007 | Shakespeare et al. |
| 2007/0153278 A1 | 7/2007 | Shakespeare et al. |
| 2008/0157013 A1 | 7/2008 | Shakespeare |

FOREIGN PATENT DOCUMENTS

| | | |
|---|---|---|
| DE | 100 31 636 A1 | 1/2002 |
| EP | 0 319 158 A1 | 6/1989 |
| EP | 0 358 575 A2 | 3/1990 |
| EP | 0 843 155 A1 | 5/1998 |
| EP | 1437222 A1 | 7/2004 |
| EP | 1457335 A1 | 9/2004 |
| EP | 1 491 877 A1 | 12/2004 |
| WO | WO 87/07381 A1 | 12/1987 |
| WO | WO 97/08537 A1 | 3/1997 |
| WO | WO 99/02941 A1 | 1/1999 |
| WO | WO 00/31521 A1 | 6/2000 |
| WO | WO 03/037111 A1 | 5/2003 |
| WO | WO 2006/116672 A2 | 11/2006 |

OTHER PUBLICATIONS

European Search Report dated Aug. 25, 2011 in connection with European Patent Application No. 11 172 011.6.

"Paper, board and pulps—Measurement of diffuse blue reflectance factor—Part 1: Indoor daylight conditions (ISO brightness)", ISO 2470-1, Oct. 1, 2009, 15 pages.

"Paper, board and pulps—Measurement of diffuse blue reflectance factor—Part 2: Outdoor daylight conditions (D65 brightness)", ISO 2470-2, Nov. 1, 2008, 9 pages.

"Paper and board—Determination of colour by diffuse reflectance—Part 1: Indoor daylight conditions (C/2 degrees)", ISO 5631-1, Oct. 15, 2009, 15 pages.

"Paper and board—Determination of colour by diffuse reflectance—Part 2: Outdoor daylight conditions (D65/10 degrees)", ISO 5631-2, Dec. 15, 2008, 12 pages.

"Paper and board—Determination of colour by diffuse reflectance—Part 3: Indoor illumination conditions (D50/2 degrees)", ISO 5631-3, Oct. 15, 2008, 12 pages.

Tarja Shakespeare et al., "Advanced Colour Control Through Reflectance Optimization", Proceedings 2nd EcoPaperTech Conference, Helsinki Finland, Jun. 1998, pp. 183-194.

Stokman et al., "Color Measurement by Imaging Spectrometry", Computer Vision & Image Understanding, San Diego, CA, US, vol. 79, No. 2, Aug. 2000, pp. 236-249.

Wandell, "Color Measurement and Discrimination", Journal of the Optical Society of America, USA, vol. 2, No. 1, Jan. 1985, pp. 62-71.

Tarja Shakespeare and John Shakespeare, "Problems in colour measurement of fluorescent paper grades", Analytica Chimica Acta, 1999, pp. 227-242, vol. 380 issue 2-3, Elsevier Science B.V., Finland.

International Search Report dated May 24, 2007 in connection with International Patent Application No. PCT/US2006/048616.

* cited by examiner

SYSTEM AND METHOD FOR ADJUSTING AN ON-LINE APPEARANCE SENSOR SYSTEM

TECHNICAL FIELD

This disclosure relates generally to web manufacturing and processing and more specifically to a system and method for adjusting an on-line appearance sensor system.

BACKGROUND

Paper, tissue, board and other so-called "web" products may be produced in a web production system controlled by a process control system. The appearance of web products produced by the web production system may be measured in a laboratory after a production run by removing one or more samples of the produced product from a machine reel holding the product. A machine reel may also be referred to as a take-up reel, or simply as a reel. The appearance of the web product may be described by measurable characteristics that include opacity, brightness, color, fluorescent properties, whiteness, gloss, and uniformity, as well as other characteristics. As used in this disclosure, the term "appearance" indicates color and/or other optically observable characteristic(s) of web products.

Typically, laboratory color measurements are made by stacking a predetermined number of sample pieces of the product and placing the stack in a measurement device. The measurement device illuminates the sample using a specified geometry with one or more light sources having specified characteristics, with or without specified filters. Light reflected and emitted from the sample product is measured under specified conditions by a sensor. A color sensor is typically calibrated using prepared calibration tiles of known properties. Such measurement parameters are typically specified by a standards-setting body, such as Commission Internationale de l'Eclairage (CIE) or International Organization for Standardization (ISO), for example ISO 2469 and ISO 5631.

Similarly, under the same or other illumination conditions, other aspects of appearance of the web product sample may be measured. Such appearance characteristics include D65 brightness, CIE whiteness, true reflectance, and apparent reflectance. Appearance of the produced product may be measured under sets of different illumination and viewing conditions, such as UV-included D65, D55, C or UV-excluded or true reflectance.

During production of a web product in a web production system, on-line sensors measure color and other appearance characteristics of the product as it is produced. Because such measurements are made from a moving web, some prerequisites of the standards-specified color measurement conditions and procedures often cannot be met. In one example, only a single sheet of product can be measured, rather than a stack of multiple layers of paper as specified in a standard. In a second example, some specified illumination and diffusion requirements may not be met by on-line appearance sensing measurement systems.

Furthermore, an online measurement system may employ an optical system having different wavelength range or wavelength response characteristics than an optical system employed in the off-line, quality laboratory measurement system. Also, physical properties of the moving web being measured in the web production system may be different than the same properties of the finished product, after conditioning to climate conditions of the quality laboratory. Such properties may include temperature and moisture content of the web product being produced.

SUMMARY

This disclosure provides a system and method for adjusting an online appearance sensor system.

In a first embodiment, a method includes receiving an on-line appearance measurement of a web of material from an on-line appearance sensor system (OnLASS) during a production run. The method further includes receiving an off-line appearance measurement of the web from an off-line appearance sensor system (OffLASS) after the production run. The method also includes comparing the on-line and off-line appearance measurements and adjusting at least one setting of the OnLASS based on the comparison. The method further includes sending the adjusted setting(s) to the OnLASS.

In a second embodiment, an apparatus includes at least one input/output circuit, and at least one processing device. The processing device is configured to receive one or more settings from an OnLASS via the input/output circuit. The processing device is also configured to receive, via the input/output circuit, an on-line appearance measurement representative of an appearance characteristic of a web of material produced during a production run. The processing device is further configured to receive, via the input/output circuit, an off-line appearance measurement representative of the appearance characteristic of the web after the production run. The processing device is also configured to compare the on-line and off-line appearance measurements and adjust at least one of the setting(s) based on the comparison. The processing device is further configured to send, via the input/output circuit, the adjusted setting(s) to the OnLASS.

In a third embodiment, a system includes an OnLASS configured to measure an appearance characteristic of a web of material produced during a production run, an OffLASS configured to measure the appearance characteristic of the web after the production run, and an error minimizer. The error minimizer is configured to receive one or more settings from the OnLASS. The error minimizer is also configured to receive an on-line appearance measurement representative of the appearance characteristic of the web from the on-line appearance sensor system. The error minimizer is further configured to receive an off-line appearance measurement representative of the appearance characteristic of the web from the off-line appearance sensor system. The error minimizer is also configured to compare the on-line and off-line appearance measurements and adjust at least one of the setting(s) based on the comparison. The error minimizer is further configured to send the adjusted setting(s) to the OnLASS.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 4, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
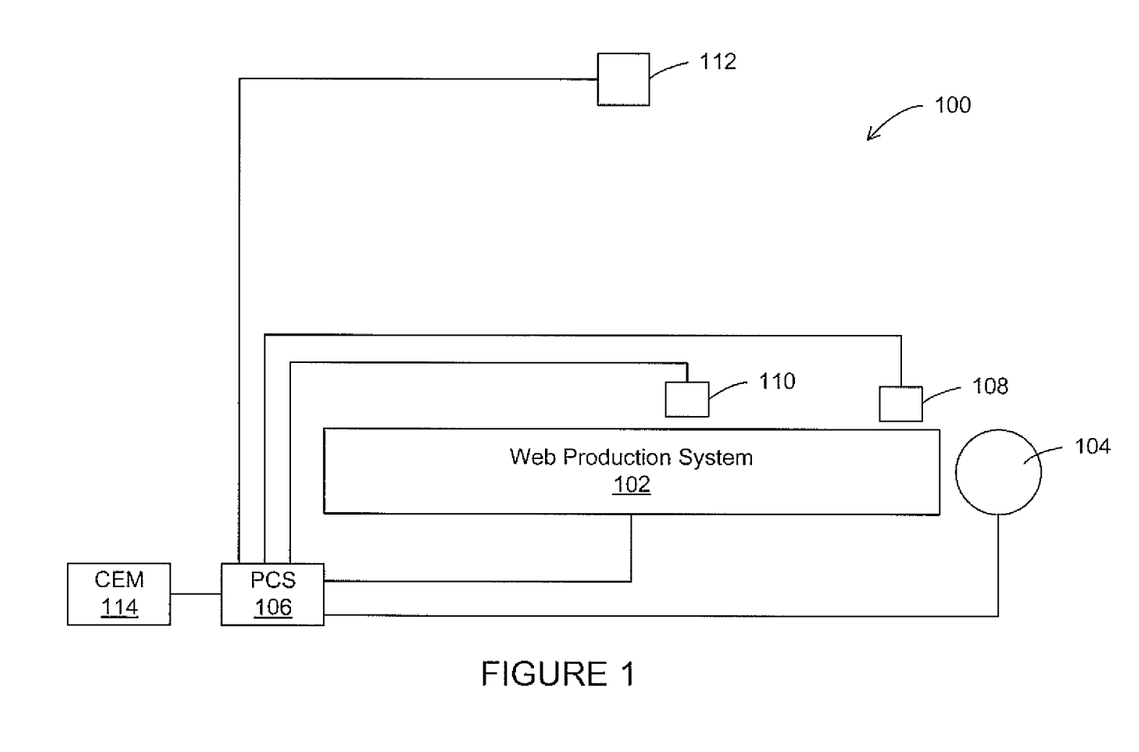
FIG. 1 illustrates an example system according to this disclosure.

FIG. 1 illustrates an example system 100 according to this disclosure. The embodiment of the system 100 shown in FIG. 1 is for illustration only. Other embodiments of the system 100 may be used without departing from the scope of this disclosure.

In this example embodiment, the system 100 includes a web production system 102, which feeds a finished web product onto a take-up reel 104. The web production system 102 could represent a paper or board machine, and the finished web product could represent a paper sheet, tissue, or board sheet. The web production system 102 and the machine reel 104 are monitored and controlled by a process control system (PCS) 106. Included in or otherwise associated with the web production system 102 are on-line appearance sensor systems (OnLASSs) 108 and 110.

In this disclosure, the term "appearance sensor system" refers to a system of one or more sensors that measure color and/or other appearance characteristic(s) of a web of material. Also, the term "settings" refers to parameters associated with an appearance sensor system, such as (i) compensation parameters of methods for estimating infinite stack measurements, (ii) compensating for production variables such as moisture and temperature, and (iii) sensor calibration parameters.

The OnLASS 108 may be located near the machine reel 104 and may measure one or more appearance characteristics of the finished web product. The OnLASS 108 may therefore be referred to as a "reel sensor." The OnLASS 110 may be located at an intermediate stage of the web production system 102 and may measure one or more appearance characteristics at that intermediate stage of production. In some embodiments, OnLASS 110 is located prior to a paper coating stage, such as prior to a blade coater, a curtain coater, size press, or a jet coater mechanism.

In particular embodiments, an OnLASS 108 may include a spectrophotometer or other spectrometer having a grating or other elements for selecting or separating light wavelengths and a detector. A spectrophotometer or spectrometer may also include optical filters, lenses and one or more light sources. The particular characteristics of the spectrophotometer or spectrometer are often a cause of differences between on-line and off-line appearance measurements.

The OnLASSs 108 and 110 are communicatively coupled to the PCS 106. The PCS 106 is configured to receive settings and measurements of color and/or other appearance characteristics from one or both of the OnLASSs 108 and 110. The PCS 106 may control elements of the web production system 102 in response to the measurements.

When a production run of a web is completed, the machine reel 104 and the product it contains are typically removed from the web production system 102, and a replacement machine reel 104 installed so that production of the web may continue. One or more portions of the product are cut from the web on the removed machine reel 104 and taken to an off-line appearance sensor system (OffLASS) 112 for measurement.

The OffLASS 112 is communicatively coupled to the PCS 106, which is configured to receive settings and measurements of color and/or other appearance characteristic(s) from the OffLASS 112.

During off-line testing, portions of the product are typically cut into pieces, and typically a specified number of pieces are formed into a stack. In general, the number of pieces in the stack represents a sufficient number of pieces such that the addition of further pieces to the stack does not produce a change in the measurement of appearance by the OffLASS 112. Color and/or other appearance of the stack can be measured by the OffLASS 112 using conditions of illumination and viewing geometry specified by one or more standards-setting bodies. In some embodiments, color measurement is expressed in user color coordinates (such as CIE L*, a*, b*) and appearance values (such as D65 brightness and CIE (D76/10) whiteness). In particular embodiments, the OffLASS 112 may include a spectrophotometer or a colorimeter. In some embodiments, a separate instrument may be used to measure brightness.

The PCS 106 is communicatively coupled to a color error minimizing (CEM) system 114. As explained below, the PCS 106 is configured to send settings and appearance measurements received from the OffLASS 112, settings and appearance measurements received from one or both of the OnLASSs 108 and 110, and information relating to the produced web on the machine reel 104 to the CEM 114. The PCS 106 is further configured to receive updated settings from the CEM 114 and to send that information to one or both of the OnLASSs 108 and 110.

While the CEM 114 is shown in FIG. 1 as a separate component of the system 100, the CEM 114 may be implemented as a part of the PCS 106. The CEM 114 may also be implemented as part of a higher-level monitoring and/or quality control system of which the PCS 106 is a part.

Figure 2:
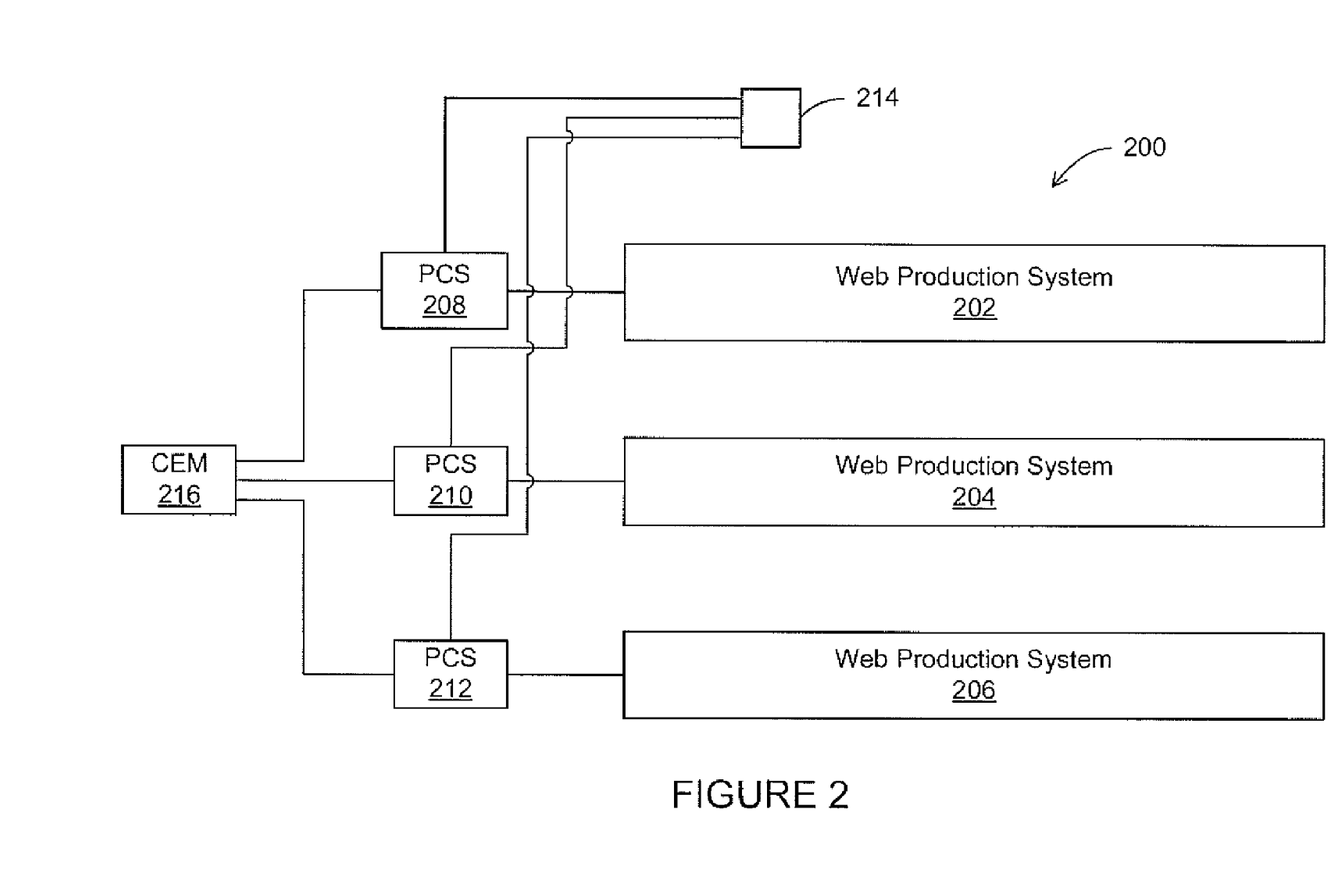
FIG. 2 illustrates another example system according to this disclosure.

FIG. 2 illustrates another example system 200 according to this disclosure. The system 200 includes multiple web production systems 202-206, which are monitored and controlled, respectively, by process control systems (PCSs) 208, 210 and 212. Each of the web production systems 202-206 includes or is otherwise associated with one or more OnLASSs (not shown in FIG. 2) for measuring color and/or other appearance characteristic(s) of a web being produced by that production system. As described above, the PCSs 208-212 are configured to receive settings and measurements of color and/or other appearance characteristic(s) from one or more OnLASSs in the associated production system 202-206. The PCSs 208-212 may control elements of the associated production system 202-206 in response to the measurements.

The production systems 202-206 are associated with an OffLASS 214, which may be used to make off-line measurements of color and/or other appearance characteristic(s) of webs produced by the production systems 202-206. The OffLASS 214 is communicatively coupled to each of the PCSs 208-212, which are configured to receive settings and measurements of color and/or other appearance characteristic(s) from the OffLASS 214.

The PCSs 208-212 are also communicatively coupled to a CEM 216. As described in more detail below, the PCSs 208-212 are configured to send information received from the OffLASS 214 and from the associated production systems 202-206 to the CEM 216. The PCSs 208-212 are further configured to receive updated settings from the CEM 216 and to send that information to one or more OnLASSs of the associated production systems 202-206.

While a stand-alone CEM 216 is depicted in FIG. 2, the CEM 216 may be implemented as a part of any one of the PCSs 208-212, which may be communicatively coupled to each other. Also, each PCS 208-212 may have an individual CEM implemented as part of the PCS, where the individual CEMS are communicatively coupled to share information relating to the settings of their on-line color sensor systems. The CEM 216 may further be implemented as part of a higher-level monitoring and/or quality control system of which the PCSs 208-212 are a part.

Note that more or fewer than three production systems may be used. Also, while two OnLASSs are described as associated with each production system 102, 202, 204 and 206, one or more than two OnLASSs may be used for measurement of a web's appearance at any number of production stages. Further, multiple OnLASSs may be used at the same stage of production to provide redundancy in the event of sensor system failure or for duplicate, confirmatory measurement readings. In addition, while only one OffLASS is shown in each of the systems 100 and 200, two or more OffLASSs may be used to increase throughput or to provide redundancy.

Typically, appearance targets of web products are referred to as "color grades." Targets of other physical properties of web products are commonly referred as "grades." Color grade and other physical properties, collectively, may also be referred to as "grade." Such physical properties may include weight, thickness, fiber blend, additives (such as ash filler), speed of making, moisture, coating (such as glossy coating or film coating), and calendaring.

Typically, a single production run by a production system 102, 202, 204 and 206 produces a single grade of product. In subsequent production runs, a production system may be used to produce the same or different grade of product as in a previous run. A production system may return to producing a certain grade of product after being used to produce one or more other grades of product. In the system 200, the production systems 202-206 may be used to produce the same or different grades of product.

As such, the OnLASSs and OffLASSs of the systems 100 and 200 may be used to measure color and/or other appearance characteristic(s) of different grades of product. The CEMs 114 and 216 according to this disclosure are operable to optimize the settings of the OnLASSs of the systems 100 and 200 both within and across product grades.

A production run typically produces web products of a single grade. A production run may produce only a single machine reel of product or may produce multiple (such as several hundred) machine reels over one or more days of production. For production runs producing multiple machine reels of products, off-line measurements of appearance may be made for each machine reel, for every second machine reel, or at any other appropriate frequency of measurement.

Figure 3:
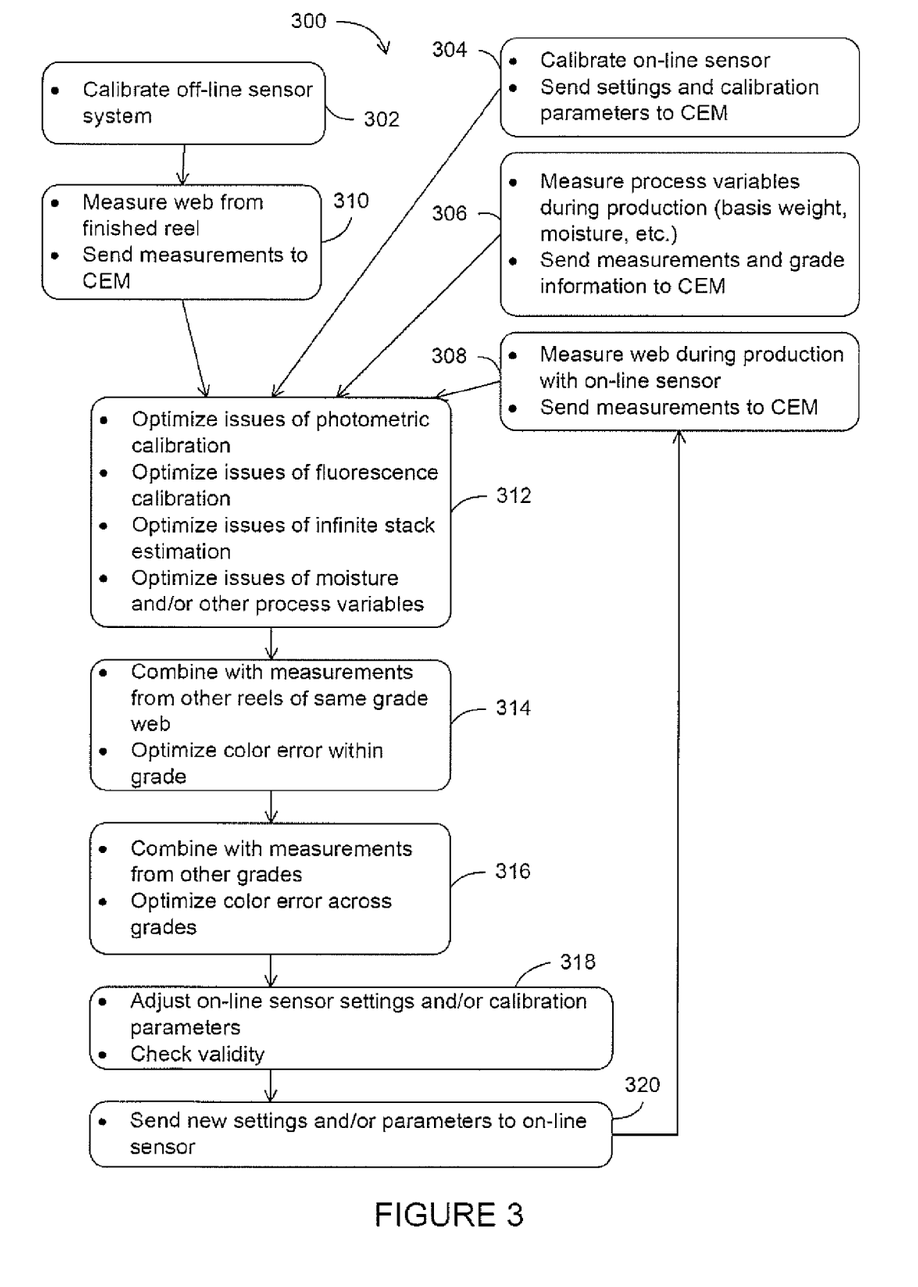
FIG. 3 illustrates an example process for calibration of an online appearance measurement system according to this disclosure.

FIG. 3 illustrates an example process 300 for calibration of an online color measurement system according to this disclosure. For ease of explanation, the process 300 is described with respect to the system 100 of FIG. 1. The same or similar process 300 could be used with other systems, such as the system 200 of FIG. 2.

In step 302, the OffLASS 112 is calibrated. Such calibration typically employs materials, procedures, and environmental conditions specified by an instrument supplier and/or measurement standards for color and/or other appearance. Such standards are intended to produce comparable measurements from measurement systems of differing configurations in differing situations. Such calibration procedures typically include methods to set photometric scales and fluorescent emission scales at specified conditions.

In step 304, the OnLASSs 108 and 110 are calibrated. Calibration procedures for the OnLASSs 108 and 110 are typically similar or identical to the calibration procedures for the OffLASS 112. The PCS 106 may store and send the calibration parameters to OnLASSs 108 and 110 at one or more specified times prior to OnLASS calibration. The calibration parameters may also be store on the OnLASS. The OnLASSs 108 and 110 send resulting calibration parameters and/or results to the PCS 106, which sends the information to the CEM 114.

During web production, in step 306, the PCS 106 may receive from other on-line or off-line sensors measurements of process variables that relate to a current production run. Such process variables may include basis weight, moisture content, web tension, web temperature, and other variables. Measured process variables, as well as information relating to the grade of product being produced, are sent to the CEM 114.

Also during web production, in step 308, the OnLASSs 108 and 110 measure color and/or other appearance of the web being produced. In particular embodiments, measurements can be made during the period that the web on the tail of the machine reel 104 is being produced. These measurements may later be compared to off-line color and/or other appearance measurements of the product. Arrangements may be made to measure the same portion of web product with both OnLASS and OffLASS, such as stopping to scan with OnLASS and transferring it to a specific fix point CD (cross directional) position of the web.

The on-line measurements of color and/or other appearance characteristic(s) are made of a fast-moving web (i.e., a single sheet), which may be translucent. An OnLASS typically employs a method to estimate the equivalent measurement of an infinitely thick stack. Such estimation methods are commonly based on the Kubelka-Munk theory or another suitable theory. On-line measurements of color and/or other appearance characteristic(s) may be affected by factors such as web tension, moisture content of paper, and temperature. An OnLASS may apply one or more methods to compensate for such characteristics. As such, compensation parameters for the OnLASSs 108 and 110 may include parameters for procedures to estimate an equivalent appearance measurement of an infinitely thick stack or to compensate for production variables such as moisture and temperature.

OnLASSs may provide not only color and/or other appearance measurements but also spectral quantities, such as true reflectance and apparent reflectance or more primitive spectral quantities and parameters used to measure or estimate true and/or apparent reflectance. Measurement values generated by the OnLASSs 108 and 110 are sent to the CEM 114.

When a production run of product is completed, or when a full machine reel is replaced with an empty reel, in step 310 the OffLASS 112 is used to measure the same region of produced product as was measured by the OnLASS 108, such as on the tail end of the machine reel 104. Such measurements are typically performed according to industry standards of color and/or other appearance measurements. These measurements may be made on a stack of paper that is sufficiently thick to simulate an infinitely thick stack of samples. In other procedures, the OffLASS 112 may measure a single sheet or few sheets of paper and may apply a method to estimate infinitely thick stack color and/or other appearance measurements.

Often, OffLASSs provide user color co-ordinates (such as CIE L*, a*, b*) and selected appearance values (such as D65 brightness, CIE (D65/10) whiteness) under selected illumination and viewing conditions and geometry. The results of the measurements by the OffLASS 112 are sent to the CEM 114. In some cases, OffLASSs may also provide spectral quantities, such as true reflectance and apparent reflectance.

In step 312, the CEM 114 optimizes compensation and/or calibration parameters of the OnLASSs 108 and 110 by comparison of the on-line color and/or other appearance measurements received from step 308 to the off-line color and/or other appearance measurements received from step 310. The process variable measurements and product grade information received from step 306 also may be used in the optimization process. Optimization may be performed to reduce non-uniformity based on static performance issues and/or dynamic performance issues between on-line and off-line sensor systems for one or more specified CIE illuminants and/or observers. Static performance issues often relate to photometric calibration and issues with measured fluorescent effects on the measurement results.

Static performance issues typically relate to differences in photometric calibration and measured fluorescent effects on the measurement results. Measured values for L* may be used to optimize photometric calibration between off-line and on-line sensor systems. Measured values for b* may be used to optimize ultraviolet (UV) energy calibration between off-line and on-line sensor systems. Measured values for Brt (brightness) may be used to optimize brightness measurement photometric and UV energy calibration between off-line and on-line sensor systems. For example, CIE (D65/10) whiteness may be used to check optimization of photometric and UV energy calibration.

Dynamic performance issues may relate to issues in the stack estimation method due to varying scattering properties within a moving web, dryness of the moving web, web tension, and other production variables that may cause grade-dependent color or other appearance measurement variations. Measured values of a*, L* and b* may be used to optimize parameters used in methods of forming an infinite stack estimate. Measured values for b* and Brt may be used to optimize parameter models to compensate for different measurement conditions between on/off-line measurements due to production variables such as moisture and temperature.

These steps provide one embodiment for combining measurements of a single production run from on-line and off-line sensor systems, as well as process variables, to optimize compensation and calibration parameters for on-line sensor systems. In step 314, on-line and off-line sensor system measurements and process variable measurements may be combined with measurements made during and after other production runs of product of the same grade. Such measurements from multiple production runs may be used to optimize compensation and calibration parameters within a single grade of product. In step 316, on-line and off-line sensor system measurements and process variable measurements may be combined with measurements made during and after other production runs of other grades of product. Such measurements from production runs of other grades of product may be used to optimize compensation and calibration parameters across multiple grades of product.

In step 318, OnLASS compensation and calibration parameters are adjusted according to the optimization calculations of steps 312-316. The adjusted settings are checked for validity and, in step 320, are sent to one or more OnLASSs 108 and 110. Such validity checks may be automatic (such as range checking) or may be performed by engineering personnel overseeing operation of the system 100. The process 300 then returns to step 308, where on-line sensor system measurements are made using the adjusted settings.

As subsequent runs of product are completed, steps 306 through 320 may be repeated to further improve compensation and calibration parameters for the OnLASSs 108 and 110. Additionally, subsequent sets of color and/or other appearance measurements may be used to improve the optimization calculations of step 312 and/or the grade optimization combinations of steps 314 and 316.

Figure 4:
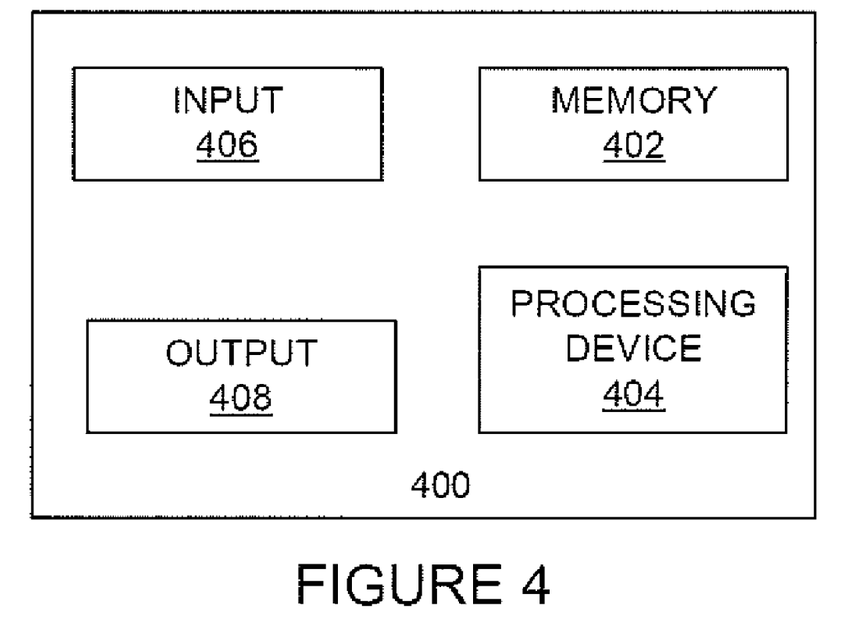
FIG. 4 illustrates an example color error minimizing apparatus according to this disclosure.

FIG. 4 illustrates an example color error minimizing apparatus 400 according to this disclosure. The apparatus 400 includes at least one memory circuit 402, at least one processing device 404, at least one input circuit 406, and at least one output circuit 408 that are configured to implement the optimization technique described above. The memory circuit 402 may be fixed or removable and includes computer code for execution by the processing device 404. The processing device 404 includes any suitable processing system or unit, such as a microprocessor, microcontroller, digital signal processor, application specific integrated circuit, or field programmable gate array. The input and output circuits 406-408 include any suitable structures for receiving or transmitting information, such as electrical terminals or wire traces.

In some embodiments, the input circuit 406 obtains compensation and/or calibration parameters from off-line and on-line appearance sensor systems, as well as production variables and product grade information. The processing device 404 combines measurements from on-line and off-line sensor systems, as well as process variables, to optimize compensation and calibration parameters for on-line sensor systems. The output circuit 408 is configured to send adjusted settings to the on-line appearance sensor systems.

While the apparatus 400 is shown using a processing device 404 and a memory 402 that includes program code, other embodiments could be used. For example, the apparatus 400 or the processing device 404 may be implemented with fixed or programmable logic configured to perform the methods of this disclosure.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The term "couple" and its derivatives refer to any direct or indirect communication between two or more elements, whether or not those elements are in physical contact with one another. Terms like "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method, comprising:
   receiving an on-line appearance measurement of a web of material from an on-line appearance sensor system taken during a production run of the web;
   receiving an off-line appearance measurement of the web from an off-line appearance sensor system taken after the production run;
   comparing the on-line appearance measurement to the off-line appearance measurement;
   identifying at least one adjusted setting of the on-line appearance sensor system based on the comparison; and
   sending the at least one adjusted setting to the on-line appearance sensor system.

2. The method of claim 1, wherein the at least one adjusted setting is identified based on at least one of a static performance issue and a dynamic performance issue associated with the on-line appearance sensor system.

3. The method of claim 1, wherein identifying the at least one adjusted setting comprises at least one of:
   optimizing photometric calibration of the on-line appearance sensor system using on-line and off-line measured values for L*;
   optimizing ultraviolet (UV) energy calibration of the on-line appearance sensor system using on-line and off-line measured values for b*; and
   optimizing brightness measurement photometric and UV energy calibration of the on-line appearance sensor system using on-line and off-line measured values for Brt.

4. The method of claim 1, wherein identifying the at least one adjusted setting comprises at least one of:
   optimizing an infinite stack estimation parameter of the on-line appearance sensor system using on-line and off-line measured values for a*, L* and b*; and
   optimizing a production variable compensation parameter of the on-line appearance sensor system using on-line and off-line measured values for b* and Brt.

5. The method of claim 1, wherein:
   the web of material has a grade; and
   the method further comprises comparing the on-line appearance measurement and the off-line appearance measurement to a second on-line appearance measurement from a second production run of the web and a second off-line appearance measurement from the second production run, the second production run associated with the same grade.

6. The method of claim 1, wherein:
   the web of material has a first grade; and
   the method further comprises comparing the on-line appearance measurement and the off-line appearance measurement to a second on-line appearance measurement from a second production run of the web and a second off-line appearance measurement from the second production run, the second production run associated with a different second grade.

7. The method of claim 1, wherein the at least one adjusted setting comprises at least one of: a compensation parameter and a calibration parameter of the on-line appearance sensor system.

8. The method of claim 1, further comprising:
   capturing sensor measurements of an additional production run using the on-line appearance sensor system with the at least one adjusted setting.

9. An apparatus, comprising:
   at least one input/output circuit; and
   at least one processing device configured to:
      receive, via the at least one input/output circuit, one or more settings of an on-line appearance sensor system;
      receive, via the at least one input/output circuit, an on-line appearance measurement from the on-line appearance sensor system, the on-line appearance measurement representative of an appearance characteristic of a web of material produced during a production run;
      receive, via the at least one input/output circuit, an off-line appearance measurement from an off-line appearance sensor system, the off-line appearance measurement representative of the appearance characteristic of the web after the production run;
      compare the on-line appearance measurement to the off-line appearance measurement;
      identify at least one adjusted setting based on the comparison; and
      send, via the at least one input/output circuit, the at least one adjusted setting to the on-line appearance sensor system.

10. The apparatus of claim 9, wherein the at least one processing device is configured to identify the at least one adjusted setting based on at least one of: a static performance issue and a dynamic performance issue.

11. The apparatus of claim 9, wherein the at least one processing device is configured to identify the at least one adjusted setting by at least one of:
   optimizing photometric calibration of the on-line appearance sensor system using on-line and off-line measured values for L*;
   optimizing ultraviolet (UV) energy calibration of the on-line appearance sensor system using on-line and off-line measured values for b*; and
   optimizing brightness measurement photometric and UV energy calibration of the on-line appearance sensor system using on-line and off-line measured values for Brt.

12. The apparatus of claim 9, wherein the at least one processing device is configured to identify the at least one adjusted setting by at least one of:
   optimizing an infinite stack estimation parameter of the on-line appearance sensor system using on-line and off-line measured values for a*, L* and b*; and
   optimizing a production variable compensation parameter of the on-line appearance sensor system using on-line and off-line measured values for b* and Brt.

13. The apparatus of claim 9, wherein:
   the web of material has a grade; and
   the at least one processing device is further configured to compare the on-line appearance measurement and the off-line appearance measurement to a second on-line appearance measurement from a second production run and a second off-line appearance measurement from the second production run, the second production run associated with the same grade.

14. The apparatus of claim 9, wherein:
   the web of material has a first grade; and
   the at least one processing device is further configured to compare the on-line appearance measurement and the off-line appearance measurement to a second on-line appearance measurement from a second production run and a second off-line appearance measurement from the second production run, the second production run associated with a different second grade.

15. The apparatus of claim 9, wherein the one or more settings comprise at least one of: a compensation parameter and a calibration parameter of the on-line appearance sensor system.

16. The apparatus of claim 9, wherein the at least one processing device is configured to send the at least one adjusted setting to the on-line appearance sensor system so that the on-line appearance sensor system is configured to capture sensor measurements of an additional production run using the at least one adjusted setting.

17. A system, comprising:
an on-line appearance sensor system configured to measure an appearance characteristic of a web of material produced during a production run;
an off-line appearance sensor system configured to measure the appearance characteristic of the web after the production run; and
an error minimizer configured to:
receive one or more settings of the on-line appearance sensor system;
receive an on-line appearance measurement representative of the appearance characteristic of the web from the on-line appearance sensor system;
receive an off-line appearance measurement representative of the appearance characteristic of the web from the off-line appearance sensor system;
compare the on-line appearance measurement to the off-line appearance measurement;
identify at least one adjusted setting based on the comparison; and
send the at least one adjusted setting to the on-line appearance sensor system.

18. The system of claim 17, wherein the error minimizer is configured to identify the at least one adjusted setting based on at least one of: a static performance issue and a dynamic performance issue associated with the on-line appearance sensor system.

19. The system of claim 17, wherein the error minimizer is configured to identify the at least one adjusted setting by at least one of:
optimizing photometric calibration of the on-line appearance sensor system using on-line and off-line measured values for L*;
optimizing ultraviolet (UV) energy calibration of the on-line appearance sensor system using on-line and off-line measured values for b*; and
optimizing brightness measurement photometric and UV energy calibration of the on-line appearance sensor system using on-line and off-line measured values for Brt.

20. The system of claim 17, wherein the error minimizer is configured to identify the at least one adjusted setting by at least one of:
optimizing an infinite stack estimation parameter of the on-line appearance sensor system using on-line and off-line measured values for a*, L* and b*; and
optimizing a production variable compensation parameter using on-line and off-line measured values for b* and Brt.

21. The system of claim 17, wherein:
the web of material has a grade; and
the error minimizer is further configured to compare the on-line appearance measurement and the off-line appearance measurement to a second on-line appearance measurement from a second production run and a second off-line appearance measurement from the second production run, the second production run associated with the same grade.

22. The system of claim 17, wherein:
the web of material has a first grade; and
the error minimizer is further configured to compare the on-line appearance measurement and the off-line appearance measurement to a second on-line appearance measurement from a second production run and a second off-line appearance measurement from the second production run, the second production run associated with a different second grade.

23. The system of claim 17, wherein the error minimizer is configured to send the at least one adjusted setting to the on-line appearance sensor system so that the on-line appearance sensor system is configured to capture sensor measurements of an additional production run using the at least one adjusted setting.

* * * * *